United States Patent [19]

Roncucci et al.

[11] Patent Number: 4,639,468
[45] Date of Patent: Jan. 27, 1987

[54] DERIVATIVES OF GLYCINAMIDE, THEIR PREPARATION AND THEIR USE

[75] Inventors: Roméo Roncucci, Paris, France; Claude L. Gillet, Blanmont, Belgium; Alexis H. Cordi, Villers-la-Ville, Belgium; Mark A. Martens, Zottegem, Belgium; Joseph L. Roba, Houyet, Belgium; Paul J. Niebes, Grez-Doiceau, Belgium; Georges E. Lambelin; William R. Van Dorsser, both of Brussels, Belgium

[73] Assignee: Continental Pharma Inc., Brussels, Belgium

[21] Appl. No.: 768,185

[22] Filed: Aug. 23, 1985

Related U.S. Application Data

[63] Continuation of Ser. No. 458,756, Apr. 21, 1983, abandoned, which is a continuation of Ser. No. 133,102, Mar. 24, 1980, abandoned.

[30] Foreign Application Priority Data

Mar. 22, 1979 [LU] Luxembourg ............................ 81068
Mar. 22, 1979 [LU] Luxembourg ............................ 81069

[51] Int. Cl.$^4$ ..................... A61K 31/16; A61K 31/165
[52] U.S. Cl. ..................... 514/620; 514/478; 514/487; 514/541; 514/542; 514/546; 514/551; 514/563; 514/616; 514/626; 560/24; 560/29; 560/30; 560/39; 560/41; 560/159; 560/169; 560/251; 562/445; 562/448; 562/561; 562/564; 564/153; 564/155; 564/158; 564/159; 564/160; 564/164; 564/165; 564/194; 564/197; 564/198
[58] Field of Search ............... 514/542, 551, 487, 478, 514/558, 563, 616, 620, 626

[56] References Cited

U.S. PATENT DOCUMENTS 2,368,208 1/1945 Epstein ............................... 560/169
2,781,385 2/1957 Spivack .............................. 562/561

FOREIGN PATENT DOCUMENTS 2637M 5/1963 France ................................ 424/300

Primary Examiner—Michael L. Shippen
Attorney, Agent, or Firm—Scott J. Meyer; James W. Williams, Jr.

[57] ABSTRACT

A glycinamide derivative of the general formula I:

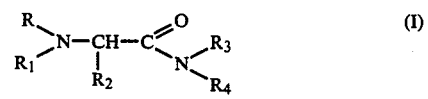

wherein:
R is a linear or ramified alkyl group $C_5$–$C_{18}$, a linear or ramified alkenyl group $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$ or $C_{18}$, a linear or ramified alkynyl group $C_4$–$C_{10}$, a linear or ramified acyl group $C_4$–$C_{18}$, a linear or ramified alkyl group $C_1$–$C_{10}$, substituted by a phenoxy group, by a hydroxy radical, by an acetoxy radical, by a carboxy radical, by a linear or ramified alkoxycarbonyl group $C_1$–$C_4$, by a carbonyl radical, by a carboxaldehyde group, by an acetal or cetal group, by one or more phenyl groups, by one or more phenyl groups substituted by a halogen atom such as fluorine, chlorine or bromine, $R_1$ represents hydrogen, a linear or ramified alkyl group $C_1$, $C_2$, $C_3$, $C_4$, $C_5$, $C_6$, $C_7$, $C_8$, $C_9$ or $C_{10}$, a linear or ramified acyl group $C_1$–$C_6$, a benzoyl group, a linear or ramified alkoxycarbonyl group $C_1$, $C_2$, $C_3$, $C_4$, $C_5$, $C_6$, $C_7$ or $C_8$, a carboxamidomethyl group, $R_2$ represents hydrogen, a linear or ramified alkyl $C_1$, $C_2$, $C_3$, a phenyl group, $R_3$ represents hydrogen, a linear or ramified alkyl group $C_1$, $C_2$, $C_3$, $C_4$, $C_5$, $C_6$, $C_7$ or $C_8$, a phenyl group, optionally substituted by a halogen atom, such as fluorine, chlorine or bromine, $R_4$ represents hydrogen, a linear or ramified alkyl group $C_1$, $C_2$, $C_3$, $C_4$, $C_5$, $C_6$, $C_7$ or $C_8$ as well as salts of these derivatives with non toxic and pharmaceutically usable acids.

5 Claims, No Drawings

DERIVATIVES OF GLYCINAMIDE, THEIR PREPARATION AND THEIR USE

CROSS-REFERENCE TO RELATED APPLICATIONS

This is a continuation of application Ser. No. 458,756, filed Apr. 21, 1983, now abandoned, which is a continuation of our earlier application Ser. No. 133,102 filed Mar. 24, 1980, now abandoned.

This invention relates to derivatives of 2-aminoacetamide currently named glycinamide, and also to salts of these compounds, their processes of preparation, pharmaceutical compositions comprising at least one of these derivatives and their method of use.

Some glycinamides are already known in chemical reactions, such as compounds of the formula:
$CH_3NHCH_2CONH_2$, $C_2H_5NHCH_2CONH_2$, $iC_3H_7NHCH_2CONH_2$, $C_4H_9NHCH_2CONH_2$, $C_6H_{11}NHCH_2CONH_2$, $C_7H_{15}NHCH_2CONH_2$, $C_6H_5NHCH_2CONH_2$, $C_6H_5CH_2NHCH_2CONH_2$, $pClC_6H_5CH_2NHCH_2CONH_2$.

Other glycinamides are known as fungicides, DOS No. 2 511 311.

Still other glycinamides are known as having pharmaceutical properties, such as compounds of the formula $C_2H_2O-CO-(CH_2)_3NH-CH_2-CONH_2$ and those described in Belgian patent No. 636.245.

One of the essential objects of this invention is to provide a class of 2-amino-acetamide derivatives having a particular interest as drugs.

Derivatives according to the invention have the general formula I:

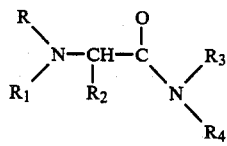

wherein: R is a linear or ramified alkyl group $C_5-C_{18}$, a linear or ramified alkenyl group $C_5-C_{18}$, a linear or ramified alkynyl group $C_4-C_{10}$, a linear or ramified acyl group $C_4-C_{18}$, a linear or ramified alkyl group $C_1-C_{10}$ substituted by a phenoxy group, by a hydroxy radical, by an acetoxy radical, by a carboxy radical, by a linear or ramified alkoxycarbonyl group $C_1-C_4$, by a carbonyl radical, by a carboxaldehyde group, by an acetal or cetal, by one or more phenyl groups, by one or more phenyl groups substituted by a halogen atom such as fluorine, chlorine or bromine, $R_1$ represents hydrogen, a linear or ramified alkyl group $C_1-C_{10}$, a linear or ramified acyl group $C_1-C_6$, a benzoyl group, a linear or ramified alkoxycarbonyl group $C_1-C_8$, a carboxamidomethyl group, $R_2$ represents hydrogen, a linear or ramified alkyl $C_1-C_3$, a phenyl group, $R_3$ represents hydrogen, a linear or ramified alkyl group $C_1-C_8$, a phenyl group, optionally substituted by a halogen atom, such as fluorine, chlorine or bromine, $R_4$ represents hydrogen, a linear or ramified alkyl group $C_1-C_8$.

According to a preferred embodiment, the invention relates to compounds of formula I, wherein: R represents a linear or ramified alkyl group $C_5, C_6, C_7, C_8, C_9, C_{10}, C_{11}, C_{12}$, a linear or ramified alkenyl group $C_5-C_{18}$, a linear or ramified alkynyl group $C_4-C_6$, a linear or ramified acyl group $C_4-C_{12}$, a linear or ramified alkyl group $C_1, C_2, C_3, C_4, C_5, C_6, C_7, C_8$ substituted by one or more phenyl groups, by one or more phneyl groups substituted by a halogen atom, such as fluorine, chlorine or bromine, by a phenoxy group, by a hydroxy radical, by an acetoxy radical, by a carboxy radical, by a linear or ramified alcoxycarbonyl group $C_1-C_4$, by a carbonyl group, by a carboxaldehyde group, $R_1$ represents hydrogen, a linear or ramified alkyl group $C_1-C_4$, a linear or ramified acyl group $C_1-C_4$, a benzoyl group, a linear or ramified alkoxycarbonyl group $C_1-C_{18}$, a carboxamidomethyl group, $R_2$ represents hydrogen, a linear or ramified alkyl group $C_1-C_3$, a phenyl group, $R_3$ represents hydrogen, a linear or ramified alkyl group $C_1-C_8$, a phenyl group, optionally substituted by a halogen atom, such as fluorine, chlorine or bromine, $R_4$ represents hydrogen.

A preferred class of products according to the invention comprises products of formula I, wherein: R represents a linear or ramified alkyl group $C_5, C_6, C_7, C_8, C_9$, a linear or ramified alkenyl group $C_5-C_{10}$, a linear or ramified alkynyl group $C_4-C_6$, a linear or ramified acyl group $C_4-C_8$, a linear or ramified alkyl group $C_1, C_2, C_3, C_4$, substituted by one or more phenyl groups, by one or more phenyl groups substituted by a halogen atom, such as fluorine, chlorine or bromine, by an acetoxy radical, by a carboxy radical, by a linear or ramified alkoxycarbonyl group $C_1-C_4$, by a carboxaldehyde group, $R_1$ represents hydrogen, a linear or ramified alkyl group $C_1-C_4$, a linear or ramified acyl group $C_1-C_4$, a carboxamidomethyl group, an alkoxycarbonyl group $C_1-C_8$, $R_2$ represents hydrogen, a methyl group, a phenyl group, $R_3$ represents hydrogen, a linear or ramified alkyl group $C_1-C_4$, a phenyl group optionally substituted by a halogen atom, such as fluorine, chlorine or bromine, $R_4$ represents hydrogen.

A particular group of products according to the invention is comprised of products of formula I, wherein: R represents a linear or ramified alkyl group $C_5, C_6, C_7, C_8, C_9$, a linear or ramified alkenyl group $C_5-C_8$, a linear or ramified acyl group $C_4-C_6$, a linear or ramified alkyl group $C_1, C_2, C_3, C_4$, substituted by a phenyl group, by an acetoxy radical, by a carboxy radical, by an alkoxycarbonyl group $C_1-C_2$, by a carboxaldehyde group, $R_1$ represents hydrogen, a linear or ramified acyl group $C_1-C_4$, an alkoxycarbonyl group $C_1-C_8$, a carboxamidomethyl group, $R_2$ represents hydrogen, an alkyl group $C_1-C_2$, a phenyl group, $R_3$ represents hydrogen, a linear or ramified alkyl group $C_1-C_4$, $R_4$ represents hydrogen.

Another preferred class of products according to the invention comprises products of formula I, wherein: R represents a linear or ramified alkyl group $C_5, C_6, C_7, C_8$, a linear or ramified alkenyl group $C_5, C_6, C_7, C_8$, a linear or ramified alkynyl group $C_5, C_6, C_7, C_8$, a linear or ramified alkyl group $C_1, C_2, C_3, C_4$ substituted by a phenyl group, by a carboxy radical, by an alkoxycarbonyl group $C_1-C_2$, by a carboxaldehyde group, $R_1$ represents hydrogen, a benzoyl group, a carboxamidomethyl group, $R_2$ represents hydrogen, an alkyl group $C_1-C_2$, a phenyl group, $R_3$ represents hydrogen, a linear or ramified alkyl group $C_1-C_4$, $R_4$ represents hydrogen.

Advantageously, the products according to the invention are of formula I wherein: R represents a linear or ramified alkyl group $C_5, C_6, C_7$ substituted by a carboxy radical, by a linear or ramified alkoxycarbonyl group $C_1, C_2, C_3, C_4$, $R_1$ represents hydrogen, a carboxamidomethyl group, $R_2$ represents hydrogen, a methyl group, a phenyl group, $R_3$ and $R_4$ are hydrogen.

Are of particular interest the derivatives of formula I wherein: R represents an alkyl group $C_2$, $C_3$, $C_4$ substituted by a phenyl group optionally substituted by a halogen atom, such as fluorine, chlorine or bromine, $R_1$ represents hydrogen, $R_2$ represents hydrogen, a methyl group, a phenyl group, $R_3$ and $R_4$ are hydrogen.

Are more particularly interesting the products of formula I wherein: R represents a linear or ramified alkyl group $C_5$, $C_6$, $C_8$, $C_9$, $R_1$ represents hydrogen, a carboximidomethyl group, an alkoxycarbonyl group $C_1$-$C_8$, $R_2$ represents hydrogen, a methyl group, a phenyl group, $R_3$ and $R_4$ are hydrogen.

A preferred sub-class is comprised of products of formula I wherein: R represents a linear or ramified alkyl group $C_5$, $C_6$, $C_8$, $C_9$, $R_1$, $R_2$, $R_3$ and $R_4$ are hydrogen.

If the derivative of formula I is as addition salts with acids, it may be transformed, according to usual processes, into free base or salts with other acids.

The most currently used salts are addition salts with acids, more particularly non toxic, pharmaceutically usable addition salts with suitable inorganic acids, for example hydrochloric acid, sulfuric acid or phosphoric acid or with suitable organic acids, such as aliphatic, cycloaliphatic, aromatic, araliphatic or heterocyclic, carboxylic or sulfonic acids, for example formic, acetic, dialkylacetic acids, such as dipropylacetic, propionic, succinic, glycolic, gluconic, lactic, malic, tartaric, citric, ascorbic, glucuronic, maleic, fumaric, pyruvic, aspartic, glutamic, benzoic, anthranilic, hydroxybenzoic, salicylic, phenylacetic, mandelic, embonic, methanesulfonic, ethanesulfonic, panthotenic, toluenesulfonic, sulfanilic, cyclohexylaminosulfonic, stearic, alginic, β-hydroxypropionic, β-hydroxybutyric, oxalic, malonic, galactaric, galacturonic acids. These salts may also derive from amino-acids, natural or not, such as lysine, glycine, arginine, ornithine, asperagine, glutamine, alamine, valine, threonine, serine, leucine, cysteine and the like.

Examples of derivatives according to the invention are:
2-n-pentylaminoacetamide,
2-n-octylaminoacetamide,
Methyl 6-(dicarboxamidomethyl)aminohexanoate,
2-n-decylaminoacetamide,
Methyl 8-(dicarboxamidomethyl)aminooctanoate,
2-n-hexylaminoacetamide,
2-(2-phenylethyl)aminocacetamide,
2-n-octadecen-9-ylaminoacetamide,
2-(N-carboxamidomethyl-N-n-hexyl)aminoacetamide,
2-(1,1-dimethylpropyn-2-yl)aminoacetamide,
Ethyl N-n-hexyl-N-carboxamidomethylcarbamate,
2-n-pentylaminobutyramide,
2-(3-phenylpropyl)aminoacetamide,
2-octen-7-ylaminoacetamide,
8-carboxamidomethylaminooctanoic acid,
2-(4-phenylbutyl)aminoacetamide,
N-n-butyl-2-[N-acetyl-N-(4-phenoxybutyl)]aminoisovaleramide.

The products of the invention may comprise one or more asymmetry centers. The products having an asymmetry center may exist as optical antipodes or a racemic or not mixture. Their separation into enantiomers, may be carried out by formation of diastereoisomer salts. For products of the invention having two asymmetry centers, two racemates corresponding to erythro and threo configurations may be obtained; these two racemates may be resolved by traditional methods, for example formation of diastereoisomer salts of action of optically active acids, such as tartaric, diacetyltartaric, tartranilic, dibenzoyltartaric, ditoluyltartaric acids and separation of the diastereoisomers by crystallization, distillation, chromatography, then liberation of the optically active bases from these salts.

The derivatives of the invention may thus be used either as mixtures containing several diastereoisomers whatever the relative proportions may be, or as enantiomer pairs in equal proportions (racemic mixture) or not, or as optically pure compounds.

The products of the invention may be used in the treatment of various forms of epilepsy, in the treatment of dyskinesiae such as parkinsonism, and in the treatment of memory troubles. Also use of some products of the invention may be provided in the treatment of psychic troubles, such as depression.

The present invention also comprises pharmaceutical compositions containing, as active ingredient, at least one compound of general formula (I) and/or salt thereof with a pharmaceutical excipient. These compositions are formulated in order to be administrated orally, rectally or parenterally.

Thus for example the compositions to be administrated orally can be liquids or solids and exist as tablets, sugar-coated pills, coated tablets, capsules, granules, powders, syrups or suspensions. The dry oral formulations comprise additives and excipients usually used in galenic pharmacy, inert diluents, disintegration agents, binders and lubricants, such as lactose, starch, talc, gelatin, stearic acid, cellulose and derivatives thereof, silicilic acid, magnesium stearate, polyvinylpyrrolidine, calcium phosphate, calcium carbonate and the like.

Such preparations can be made in order to prolong disintegration and consequently the active duration of the active element.

The aqueous suspensions, the emulsions and the oily solutions are prepared in the presence of sweetening agents, such as dextrose or glycerol, flavouring agents, such as vanillin for example, and can also contain thickening agents, wetting agents, preservation agents.

The oily emulsions and solutions are prepared in an oil of vegetal or animal origin and can contain emulsifier, flavouring, dispersing, sweetening and antioxidant agents. For parenteral administration, sterile water, an aqueous polyvinylpyrrolidone solution, peanut oil, ethyl oleate and the like are used as a vehicle. These aqueous or oily injectable solutions can contain thickening, wetting, dispersing and gelling agents.

The products of the invention may be prepared by various processes such as for example those hereinafter described.

Process A

According to this way of proceeding, amine II is converted in glycinamide of formula I.

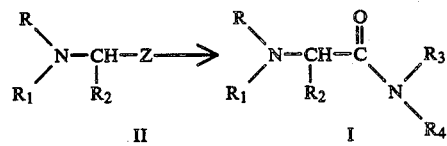

wherein $R_1$, $R_1$, $R_2$, $R_3$ and $R_4$ are such as hereinabove defined and Z is a function which by action of a suitable reactant may be transformed in amide function, for example the carboxylic acid function (—COOH), the nitrile function (—CN), the ester function (—COOR$_5$, where R$_5$ is a lower alkyl radical C$_1$-C$_3$ or a substituted phenyl radical so that it activates ester with respect to the attack of a nucleophile), an amidine function:

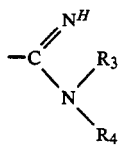

an acid halide function:

where X represents a halogen atom such as chlorine or bromine, or still an anhydride function. Z may also represent a carboxylic acid precursor such as for example the trichloromethyl group or an oxazoline:

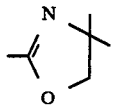

The passage of product II to product I, namely conversion of an amide precursor into amide is made by traditional reactions well known in chemistry, such as for example:

(a) Conversion of carboxylic acid into amide.

Several processes allow this chemical transformation to be made. For example, the carboxylic acid may be brought in the presence of the amine, the pyrolysis of the salt so formed leads to the amide, as well as the action of a dehydrating agent, such as P$_2$O$_5$. Another way of proceeding consists of transforming the carboxylic acid into acid halide, then into amide by action of an amine. The conversion of the acid into acid halide is very often made without solvent with thionyl chloride, phosphorus pentachloride or phosphorus oxychloride. The corresponding bromides may also be used. In order the reaction be complete, it is often useful to heat the reaction mixture to a temperature between 50° and 150° C. If a solvent is useful for the reaction development, it will be an inert organic solvent, such as hydrocarbons, for example benzene, toluene or petroleum ether or ethers such as diethyl ether.

The reaction between acid halide and amine is carried out by cooling the reaction mixture to a temperature between 0° C. and —50° C., adding an amine excess (at least 2 equivalents, or at least 1 equivalent of amine and at least 1 equivalent of a tertiary organic base, such as for example triethylamine). Traditionally, the acid chloride is added to the amine as a solution in an inert organic solvent, such as those hereinabove defined or still as a solution in water.

Still another way of proceeding consists of reacting a carboxylic acid and an amine in the presence of a coupling agent such as used for example in peptide synthesis. Presently a large number of coupling agents exist such as for example dicyclohexylcarbodiimide, N-ethyl-N',3-dimethylaminopropylcarbodiimide, phosphinies, phosphites, silicium tetrachloride or titanium tetrachloride.

(b) Conversion of a nitrile into amide.

The nitriles may be hydrolyzed into amides either in acid medium or in basic medium.

If hydrolysis is made under acid conditions, one may use concentrated sulfuric acid, aqueous concentrated hydrochloric acid, formic acid in the absence of solvent, acetic acid in the presence of boron trifluoride. In most cases, it is advantageous to heat the reaction mixture at temperatures which may reach 200° C. Another way of conversion of a nitrile into amide, in acid medium, consists of treating said nitrile with hydrochloric acid in an alcohol such as ethanol. An intermediate iminoether is thus formed, which is thermally transformed into amide.

If hydrolysis is made under basic conditions, in such a case an aqueous solution of a alkaline or alkaline-earth metal hydroxide is used. Advantageously, the presence of hydrogen peroxide improves the hydrolysis reaction. The applicant has formed an original process for hydrolysing nitrile, consisting of adding 1 equivalent of cupric chloride to 1 equivalent of nitrile and providing the reaction in an aqueous solution of an alkaline metal hydroxide at pH=10 preferably at room temperature. Again, it is often advantageous to carry out the hydrolysis reaction at a temperature between normal temperature and reflux temperature of the reaction mixture. Another very traditional method of basic hydrolysis of nitriles develops by using alkaline metal hydroxide, preferably potassium hydroxide in t-butanol.

(c) Conversion of an ester into amide.

The aminolysis of an ester is traditionally made either in water or in an inert organic solvent. As example of usable solvent, one may mention an aromatic hydrocarbon, such as benzene or toluene, an aliphatic hydrocarbon such as hexane or petroleum ether, a halogenated hydrocarbon such as dichloromethane, or chloroform. The presence of a strong base may be essential in the case of reaction with not very basic or sterically hindered amines. The above reaction may be led at a temperature between room temperature and reflux temperature of the solvent.

(d) Conversion of an amidine into imide.

The reaction is mainly carried out by acid hydrolysis in aqueous or alcoholic medium. The acid may be inorganic such as hydrochloric acid or sulfuric acid, or oorganic such as acetic acid. The reaction takes place at a temperature between room temperature and reflux temperature of the reaction mixture.

When the group Z of the general formula is a carboxylic acid precursor, the transformation into carboxylic acid is made either in water, or in an inert organic solvent in the presence of acid. By inert organic solvent is meant a solvent such as an aromatic or aliphatic hydrocarbon, chlorinated or not, for example benzene, toluene, chloroform, dichloromethane or an ether such as diethyl ether, tetrahydrofuran or dioxane. As acid, a mineral acid is generally used, such as halogen hydracids, concentrated or diluted sulfuric acid, concentrated or diluted nitric acid, phosphoric acid or an organic acid such as acetic acid. The reaction temperature is comprised between 0° C. and 150° C. and preferably between 50° C. and 100° C.

In some cases, it may be advantageous not to make the direct transformation of Z into amide:

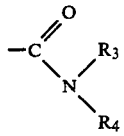

but to transform a value of Z into another value before to generate the amide function. The processes allowing these transformations to be made are well known in the art and they will be quickly reviewed.

transformation of an acid into an ester and vice versa

The esterification of an acid is a very general reaction which may develop in various ways. Traditionally, the acid and alcohol are reacted in the presence of an acid catalyst such as hydrochloric acid or sulfuric acid or p-toluenesulfonic acid. This reaction is advantageously made under anhydrous conditions and one of these reactants is used in a large excess. The solvent may be either one of the reactants, or an inert organic solvent such as chlorinated hydrocarbons, for example chloroform or carbon tetrachloride or an aromatic or aliphatic hydrocarbon, such as benzene, toluene or petroleum ether. The temperature is between normal temperature and the reflux temperature of the reaction mixture.

Another way of proceeding consists of distilling out water as soon as formed by using a suitable apparatus. The reaction conditions are identical to those hereinabove described except that one of the reactants must not be used in a large excess.

The hydrolysis of the ester is made under similar conditions as for the esterification reaction but in this case, one of the reactants, water in this event, is used in a very large excess. The catalysis and temperature conditions are the same as for esterification.

transformation of a nitrile into an ester

The transformation of a nitrile into an ester is made by opposing this nitrile to an alcohol in acid medium. Many catalysts have been described such as hydrochloric acid, hydrobromic acid, hydroiodic acid, sulfuric acid p-toluenesulfonic acid and napthalenesulfonic acid. The alcohol may be used as a solvent or one may use any other inert organic solvent such as chlorinated hydrocarbons or aliphatic or aromatic hydrocarbons. The reaction develops at a temperature between normal temperature and the reflux temperature of the solvent. Thus an intermediate iminoether is formed, which is converted into ester by hydrolysis.

transformation of a nitrile into an acid

The hydrolysis of a nitrile into carboxylic acid is carried out in acid medium or basic medium. As acid, generally a halogen hydracid is used such as hydrochloric acid or hydrobromic acid, or an oxacid such as sulfuric acid or nitric acid. As base, an alkaline hydroxide such as sodium hydroxide or potassium hydroxide is used. This hydrolysis develops in water and under reflux for several hours.

transformation of a nitrile into amidine

The conversion of a nitrile into amidine is made by reacting the nitrile with an amine. It is often advantageous to activate one of the reagents so as to obtain amidine with a better yield. An activated form of nitrile may be an iminoether or still an imino halide. The amine may be activated as a salt with an alkaline or alkaline-earth metal. Under these conditions, the amidines are obtained with good yields.

In order that the process be better understood, the main way of obtaining derivatives II are described hereinafter.

I Synthesis of compound II

1. The derivative I may be obtained from the product III by alkylation or acylation

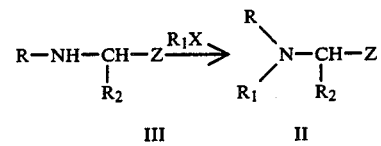

R, $R_1$ and $R_2$ are such as previously defined but however in this case $R_1$ does not represent hydrogen. X represents a good nucleus repellent, such as a halogen, for example chlorine, bromine or iodine, a tosyl or mesyl group or an acyloxy group. The reaction may be made in an organic solvent, such as chloroform, dichloromethane, in an alcohol such as methanol or ethanol, in a saturated or aromatic hydrocarbon, such as petroleum ether, benzene, toluene. The reaction develops either at room temperature or at a temperature between 0° C. and the reflux temperature of the solvent. Advantageously, the reaction may be made in the presence of an organic base, such as triethylamine, pyridine or N-dimethylaniline, or of an inorganic base, such as alkaline or alkaline-earth metal hydroxides, carbonates and bicarbonates or of finely pulverized lime.

A variant of this process is illustrated hereinbelow:

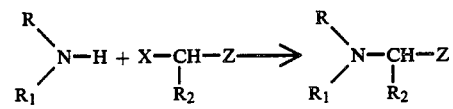

It will be noted that the above reaction and the preceding one are two reactions of alkylation or acylation of a secondary amine into a tertiary amine. It is obvious that the operation conditions for these two reactions are quite comparable.

If in the product of the invention which is desired, R and $R_1$ represent an alkyl radical and if the substituent $R_1$ has been brought by acylation of the amine, the amide so formed has to be reduced into amine. Numerous processes have been described for carrying out such a reduction; as examples mention may be made of the hydrogenation in the presence of Raney nickel or cupric chromite in inert solvents such as lower alcohols, for example methanol or ethanol, or still acetic acid; and of the reduction with lithium aluminium hydride in ethers such as diethyl ether, tetrahydrofuran or dioxane.

It is obvious that in the selection of conditions of reduction, account has to be taken that it is necessary to retain the functionality of the group Z.

2. A variant which is only valid when Z represents a nitrile (—CN) may be schematized as follows:

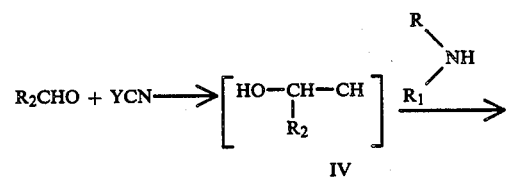

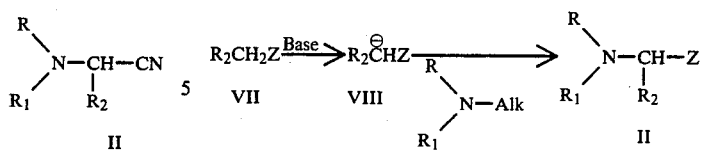

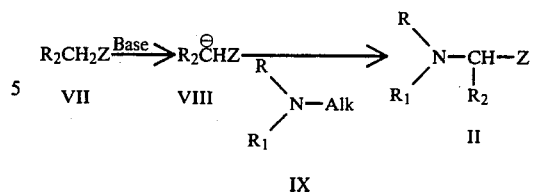

R, $R_1$ and $R_2$ are such as hereinabove defined and Y represents a cation and is such as more particularly defined hereinbelow.

Cyanohydrin IV used as co-reagent may be presynthetised or formed in situ from an aldehyde ($R_2$CHO) or an inorganic or organic cyanide, such as sodium or potassium cyanide or trimethylsilyl cyanide or still alkyl aluminium or alkyl ammonium cyanide.

The condensation of the amine on cyanohydrin is made in inert organic solvent, such as chlorinated hydrocarbons, for example chloroform or dichloromethane, or an aromatic or aliphatic hydrocarbon, such as benzene, toluene or petroleum ether, or still an ether such as diethyl ether or dioxane. In order to obtain a good yield, it is sometimes advantageous to work at a temperature between 20° C. and 120° C.

An acid catalyses the reaction: a halogen hydracid will for example be selected, such as hydrochloric acid, or an oxyacid, such as sulfuric acid, or an organic acid, such as p-toluenesulfonic acid.

The reaction between an iminium salt V and a cyanide VI occurs in the same way.

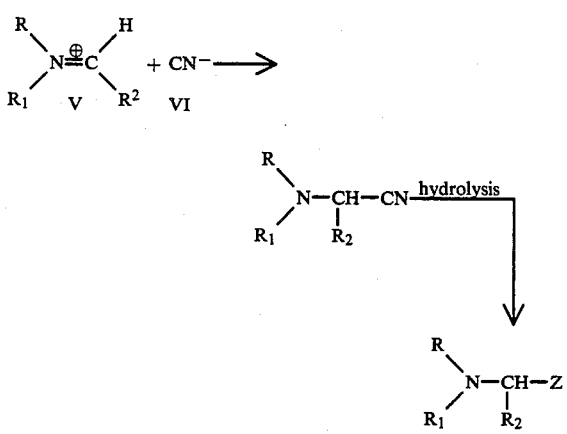

R, $R_1$, $R_2$ and Z are such as previously defined.

The addition of cyanide VI to the iminium salt V is made in an inert organic solvent, such as chlorinated hydrocarbons, for example chloroform or dichloromethane, or an aromatic or aliphatic hydrocarbon, such as benzene, toluene or petroleum ether. It is advantageous to operate at a temperature between 0° C. and the reflux temperature of the solvent. According to the hydrolysis conditions, Z will be a carboxylic acid, an amide, an ester or an amidine.

3. A third variant allowing to obtain the derivative II is represented by the following schema:

R, $R_1$, $R_2$ and Z are such as defined for the general formula and in the preceding processes, while Alk represents a lower alkyl radical $C_1$-$C_4$.

The derivative VII is transformed into anion VIII with a strong base in an inert organic solvent. The used base may be an alkoxide, such as potassium, t-butoxide, or an amide such as sodium or lithium amide, or still a complex base, currently named "base of Caubere" and which is a mixture of amide and alkoxide. The organic solvent is an aromatic or aliphatic hydrocarbon, such as benzene, toluene or petroleum ether. The reaction temperature may be comprised between −20° C. and the reflux temperature of the solvent according to the reactivity of the substrate.

The anion of derivative VII is then brought together with O-alkylated derivative of hydroxylamine IX so as to form product II. This substitution reaction is made in an inert organic solvent and at a temperature between −20° C. and the reflux temperature of the solvent.

4. According to this way of proceeding, which is only valid in the case of Z representing the nitrile group (—CN), the derivative II is obtained from an enamine X by addition of hydrocyanic acid.

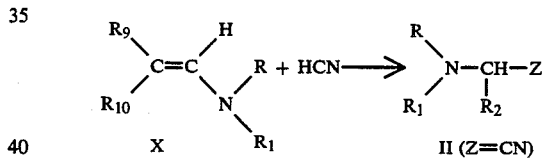

R, $R_1$ and $R_2$ have the meanings such as previously defined while:

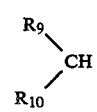

represents the substituent $R_2$.

The hydrocyanic acid may added as such or formed in situ. This reaction of addition is made in inert organic solvent, preferably slightly polar, such as chlorinated hydrocarbons, for example chloroform or dichloromethane or still in acetonitrile and at a temperature between room temperature and the reflux temperature of the solvent.

5. This process consists of reducing the double bond carbon-carbon of a α-cyanoenamine XI

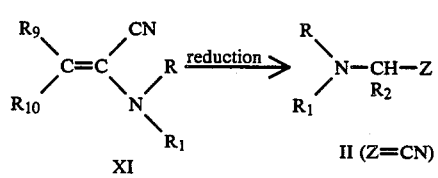

R, $R_1$ and $R_2$ are such as defined for the general formula and:

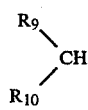

represents the substituent $R_2$.

The reduction of the double bond carbon-carbon is traditionally made by hydrogenation in the presence of a catalyst of the group comprising transition metals, their oxides or their sulfides on an inert support. As catalysts may be mentioned nickel Raney, platinum, platinum oxide or palladium on carbon. The presence of a solvent is wished and it is selected from the group comprising lower alcohols such as methanol or ethanol or still from the group comprising glacial acetic acid and simple esters thereof. The reduction is made at ordinary pressure or at a higher pressure. The reduction may also be made with hydrides such as sodium borohydride, advantageously in the presence of a Lewis acid or with diborane in solvents such as methanol, ethanol, diglyme, tetrahydrofuran or dioxane. The reduction conditions must be suitably selected so as to retain the nitrile group.

It is also to be noted that the recent prior art describes some very general ways of obtaining α-cyanoenamines XI.

II Synthesis of a compound III

The reagent II which is the starting material for the first synthesis process of glycinamides according to the invention may be obtained according to various methods.

1. A first synthesis method and its variant are to compare with alkylation or acylation of the secondary amine into tertiary amine such as described in paragraph I.1

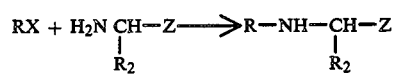

or

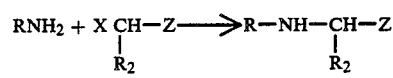

R, $R_2$ and Z have been defined previously while the nature of X has been precised in process I.1.

Alkylation or acylation of primary amine into secondary amine develop in the same way and substantially under the same conditions as alkylation and acylation of a secondary amine in tertiary amine; the experimental conditions described in the paragraph I.1 may easily and successfully been applied to the present reaction.

2. A valuable variant only when Z represents a nitrile group (CN) is illustrated by the following scheme:

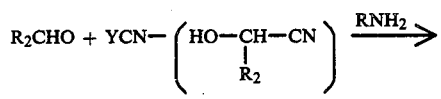

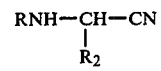

R and $R_2$ are such as hereinabove described and Y has the same meaning as in paragraph I.2. This process is very similar to the process described in paragraph I.2, at the only difference that the amine involved is in the present case a primary amine instead of a secondary amine. This only difference is not critical for the definition of operation conditions so that conditions described in paragraph I.2 may be applied successfully for carrying out the present process.

3. A third method of obtaining derivative III which is similar to that which has been described in paragraph I.3 may be schematized as follows:

R, $R_2$ and Z are such as previously defined while Alk has been defined in process I.3 as being a lower alkyl radical $C_1$-$C_4$.

The requirements as well for solvent as for base and temperature for this reaction have been defined in paragraph I.3.

4. Another way of obtaining derivative III is characterized by formation of an intermediate imine XII obtained from an amine and a carbonyl compound XIII. The reduction of the imine leads to derivative III.

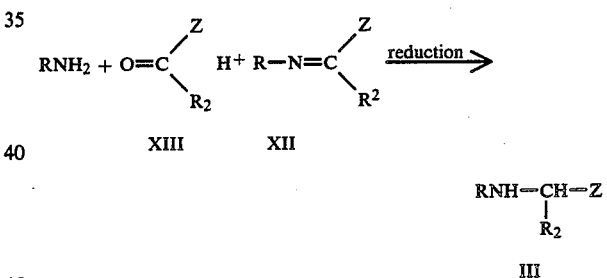

The condensation between the amine and carbonyl derivative XIII is traditionally made in an inert organic solvent, preferably water immiscible, such as benzene or toluene. Advantageously, the reaction is catalysed by an organic or inorganic acid. The p-toluenesulfonic acid is very currently used to play this catalystic role. The imine so obtained is traditionally reduced into amine.

The reduction is made in the presence of hydrogen and a hydrogenated catalyst, such as platinum, platinum oxide or palladium on charcoal in a solvent such as methanol, ethanol, ethyl acetate or glacial acetic acid, at room temperature or more advantageously at a higher pressure, or still with an alkaline metal hydride such as sodium borohydride in a solvent such as methanol or aluminium and lithium borohydride, in a solvent such as ether or tetrahydrofuran.

It is obvious that the reduction method of the imine will be selected so as to maintain intact the functionality of the group Z. By selecting different reagents, a variant of the process may be illustrated, which allows to obtain product III through intermediates bearing the same chemical functions as hereinabove.

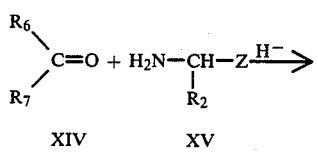

XIV     XV

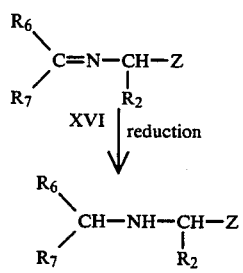

XVI | reduction $R_2$ and Z have the hereinbefore given meaning while groups $R_6$ and $R_7$ have such values as

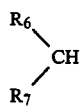

is equivalent to R.

The condensation of the carbonyl derivative XIV on amine XV and the reduction of imine XVI are made under conditions such as hereinabove described.

5. According to this synthesis method, which is acceptable only when Z represents a carboxy group (—COOH), a derivative of creatinine XVII is brought into the presence of an aldehyde XVIII, the product XIX so obtained is then reduced and hydrolysed into a derivative III.

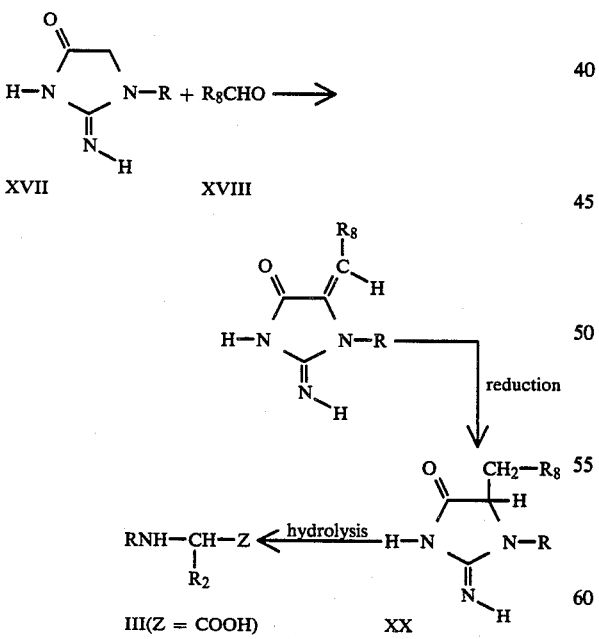

In this scheme, R, $R_2$ and Z have the hereinabove defined meanings while substituent $R_8CH_2$ represents the values of radical $R_2$.

The condensation of aldehyde XVIII on the heterocyclic compound XVIII is made in an inert organic solvent such as chlorinated hydrocarbons, for example chloroform or dichloromethane, lower alcohols such as methanol or ethanol, aromatic or aliphatic hydrocarbons, such as benzene, toluene or petroleum ether, aliphatic or cyclic ethers or still dimethylformamide.

The reaction temperature may be selected from a broad range of temperatures but this reaction is usually made at a temperature between room temperature and 100° C.

The presence of a base is essential to the development of the reactions. This base may be an inorganic base, such as alkine or alkaline-earth metal hydroxides, or an organic base such as pyridine, triethylamine, or the salt of a carboxylic acid such as sodium acetate.

The reduction of the carbon-carbon double bond of compound XIX is made in a traditional way by hydrogenation in the presence of a catalyst from the groups of transition metals, their oxides or their sulfides or an inert support. As catalysts may be cited Raney nickel, platinum, platinum oxide or still palladium on charcoal. The presence of a solvent is advisable and it is selected from lower alcohols such as methanol or ethanol or still from the group comprising glacial acetic acid and simple esters thereof. This reduction is made at ordinary pressure or at a higher pressure. The reduction may also be made with hydrides such as sodium borohydride, advantageously in the presence of a Lewis acid or with diborane in solvents such as methanol, ethanol, diglyne, tetrahydrofuran or dioxane.

The hydrolysis of the derivative XX is made in aqueous medium or in an inert organic solvent. The presence of an acid is essential to this reaction. The acid may be inorganic such as hydrochloric acid or sulfuric acid, or organic, such as acetic acid or p-toluenesulfonic acid.

By modifying the starting heterocycle, one may obtain derivative III which keeping the reaction sequence and experimental conditions. Thus one may start from hydantoin XXI, a thiodihydantoin XXII, a dioxopiperazine XXIII or a 2-thiono-5-oxathiazolidine XXIV.

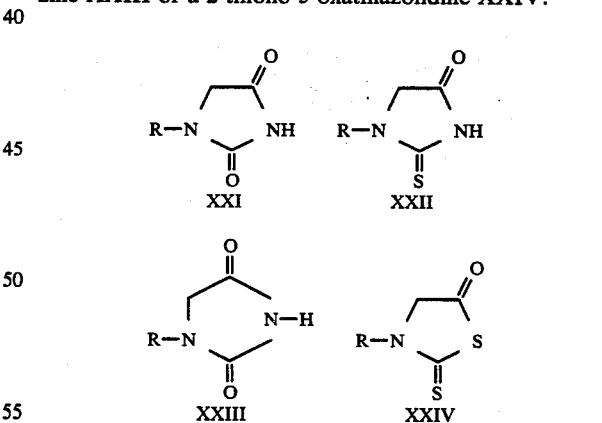

6. Another way of obtaining product III, also only valid when Z represents a carboxy group (—COOH) uses an amine and a α-carbonyl aldehyde XXV according to the scheme:

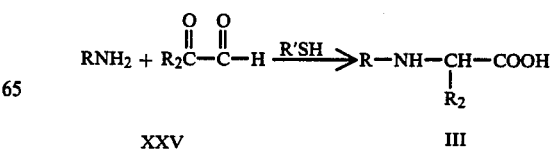

The oxydising-reducing amination of the glyoxal compound XXV is made either in aqueous solution, or in an inert organic solvent selected for example from chlorinated hydrocarbons, such as chloroform or dichloromethane, or from lower alcohols, such as methanol or ethanol, or still from aromatic or aliphatic hydrocarbons, such as benzene, toluene or petrolum ester. The reaction is generally made at a temperature between room temperature and the reflux temperature of the solvent.

Advantageously, a thiol (R'SH) will be added to the reaction mixture as catalyst (R' represents a lower alkyl radical $C_1$-$C_4$ or a phenyl ring).

Process B

This process consists of a hydrogenolysis of a sydnonimine XXVI according to the following reaction scheme:

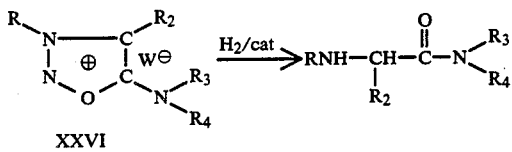

XXVI

R has the hereinabove given meaning and $W^\ominus$ represents an anion such as a halide, a sulfate, a nitrate, a phosphate or an anion deriving from an organic radical such as an acetate.

The sydnonimine is synthetised according to well known prior art documents; its hydrogenolysis leads to a 2-aminoacetamide.

The used catalyst may be palladium on active charcoal, nickel, platinum oxide. Generally, the catalyst is from the group of transition metals, their oxides or their sulfides.

The reaction solvent may advantageously be methanol, ethanol, petroleum ether or any organic solvent which is inert in the reaction conditions. The reaction usually develops at room temperature but the temperature may be adapted to the molecule reactivity either by increasing or lowering it.

Process C

According to this process, an aldehyde or an amine are opposed to an isonitrile XXVII in the presence of a carboxylic acid.

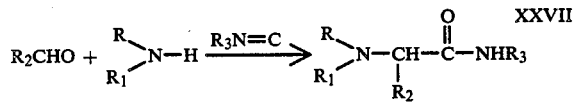

R, $R_1$, $R_2$ and $R_3$ are such as hereinabove defined.

The condensation of the amine on the aldehyde is made under the same general conditions as for the imine synthesis. These conditions have been described in paragraph II.4.

The addition of isonitrile is made in an inert organic solvent such as aromatic or aliphatic hydrocarbons, such as benzene, toluene or petroleum ether, or chlorinated hydrocarbons, such as chloroform or dichloromethane, or ethers, which are cyclic or not.

The temperature at which the reaction develops is adapted to the reagent reactivity; if the reaction is strongly exothermal, it may be useful to cool the reaction mixture in an ice bath or in a refrigerating bath based for example on dry ice; if on the contrary the reaction is very slow, it may be necessary to increase the temperature up to reflux.

A variant of this process consist of firstly reacting aldehyde and isonitrile XXVII and then to open the intermediate iminooxirane XXVIII by the amine.

$R_2CHO$ +

XXVII

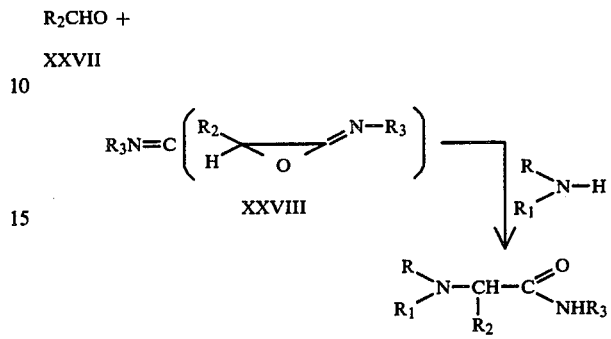

The reaction between aldehyde and isonitrile is preferably made at very low temperature (between $-30°$ C. and $-100°$ C.) and is advantageously catalysed with a Lewis acid such as, for example, $BF_3$ etherate. An ether, such as diethylether, quite well meets the reaction requirements. To prevent any moisture trace, the reaction is made in a nitrogen or argon atmosphere.

The opening of the imino-oxirane XXVIII is made by addition of amine to the reaction mixture at low temperature, then gradually raising the temperature to room temperature.

By using an optically active amine to open iminooxirane, it is possible to obtain preferably one of the glycinamide enantiomers with a non negligible optical yield.

It is still to be noted that the imino-oxirane XXVIII may be synthetised by oxydation of cetenimine XXIX. The currently used oxidising agent is m-chlorobenzoic acid (mCPBA).

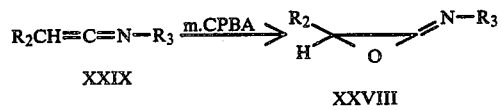

XXIX XXVIII

Process D

According to this way of proceeding, a secondary amine $RR_1NH$ is reacted with glyoxal XXX so as to form a glycinamide.

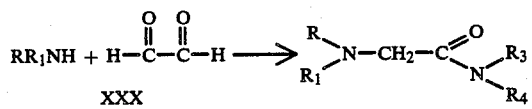

XXX wherein R and $R_1$ are such as previously defined while $R_3$ and $R_4$ have the same values as R and $R_1$.

This reaction proceeds in two steps. First an exothermal reaction develops when reagents are contacted. Then, to obtain the desired glycinamide, the temperature of the the reaction mixture or of the resulting solid has to be increased till about 150° C., advantageously till the reflux temperature. This reaction proceeds without solvent or in an inert organic solvent, such as aromatic aliphatic hydrocarbons, such as benzene, toluene or petroleum ether, or still in chlorinated solvents, such as chloroform or carbon tetrachloride. If use of a base is necessary, an inorganic base will be preferably used, such as alkaline or alkaline-earth metal hydroxides or oxides, such as quick lime or sodium hydroxide, or still a carbonate such as potassium carbonate.

Hereinafter are given detailed preparation examples of some glycinamide derivatives according to the invention. These examples have more particularly for their object to more fully illustrate the particular characteristics of the process according to the invention.

EXAMPLE 1

Synthesis of 2-n-octadecylaminoacetamide

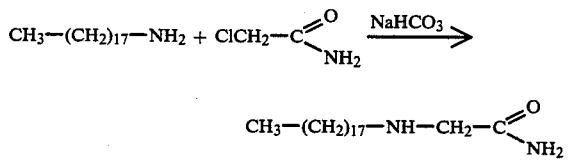

In an Erlenmeyer flask of 500 ml, provided with a cooling system and a magnetic stirrer, 21.6 gr ofoctadecylamine (0.08 mol), 7.48 gr of chloroacetamide (0.08 mol) and 7.4 gr of sodium bicarbonate were mixed in 350 ml of methanol at room temperature. This mixture was refluxed for 16 hours. After cooling of the solution, the solid was filtered and the solution was evaporated. The evaporation residue and the solid previously filtered were brought together and recrystalized from cyclohexane. A sublimation at 120°–140° C. under $5.10^{-3}$ mm of Hg, followed by a new recrystallization from cyclohexane allowed to obtain an analytically pure product.

MP (°C.): 102.5°–103.5° C.

| Analysis | C | H | N |
| --- | --- | --- | --- |
| % calculated | 73.56 | 12.96 | 8.57 |
| % found | 73.4 | 12.7 | 8.55 |

EXAMPLE 2

Synthesis of 2-n-hexylaminoacetamide

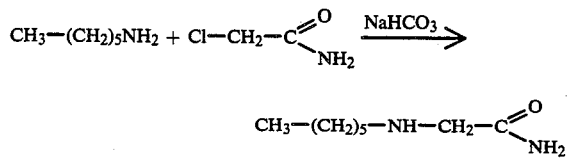

In an Erlenmeyer flask of 500 ml, provided with a refrigerating system and a magnetic stirrer, 11 gr of hexylamine (0.11 mol), 10 gr of chloroacetamide (0.107 mol) and 9.9 gr of sodium bicarbonate (0.118 mol) were mixed in 200 ml of ethanol at room temperature. This mixture was refluxed for 24 hours. After cooling, sodium chloride was filtered and the product was washed with 50 ml of ethanol.

The combined filtrates were evaporated and the white solid as obtained was recrystallized once from 140 ml of cyclohexane, once from 120 ml of acetone, finally from a minimum of ethyl acetate. The so obtained product was sublimed at 120° C. under $3.10^{-3}$ mm Hg and again recrystallized from 110 ml of cyclohexane.

MP (°C): 62–63.

| Analysis | C | H | N |
| --- | --- | --- | --- |
| % calculated | 60.72 | 11.46 | 17.71 |
| % found | 60.60 | 11.2 | 17.4 |

EXAMPLE 3

Synthesis of methyl 5-(carboxamidomethyl)amino-hexanoate

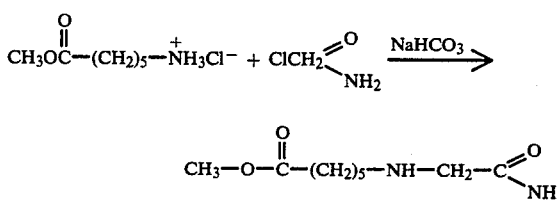

In an Erlenmeyer flask of 250 ml provided with a cooling system and a magnetic stirrer, 22 gr of hydrochloride of methyl ester of 6-aminocaproic acid (0.121 mol) and 21 gr of sodium bicarbonate (0.250 mol) were mixed in 200 ml of isopropanol. This mixture was refluxed for 1 hour and then 11.22 gr of chloroacetamide (0.120 mol) were added at room temperature. The suspension was agitated for 4 days at room temperature, the obtained precipitate was filtered and washed with 50 ml of boiling ethanol and the combined filtrates were evaporated. The residue was chromatographed in 1000 gr of silica by eluting with a methanol-ether mixture (4/6). The product was collected between the 25th and 58th fraction of 50 ml. It was finally purified by dissolving in isopropanol and saturation of the so obtained solution with HCl. An additional recrystallization from isopropanol gave an analytically pure product.

MP (°C.): 160°.

| Analysis | C | H | N |
| --- | --- | --- | --- |
| % calculated | 45.28 | 8.02 | 11.73 |
| % found | 45.00 | 8.05 | 11.73 |

EXAMPLE 4

(a) Synthesis of dodecylaminoacetonitrile

In a flask of 500 ml provided with a magnetic stirrer, 4.56 gr of hydroxyacetonitrile (0.08 mol) were mixed at room temperature with 16.3 gr of dodecylamine (0.088 mol) in 250 ml of methanol. The mixture was allowed to stand for 16 hours at room temperature and methanol was evaporated. The obtained liquid was distilled under $10^{-2}$ mm Hg. The fraction distilling between 106° and 116° crystallizes after cooling.

MP (°C.): 28°–29°.

(d) Synthesis of 2-n-docecylaminoacetamide

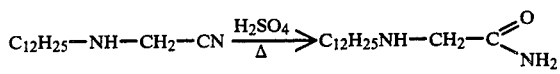

15.2 gr of dodecylaminoacetonitrile (0.068 mol) dissolved in 20 ml of ethanol were dropwise added to 2.5 ml of $H_2SO_4$ in 25 ml of ice-cooled ethanol. The white precipitate which formed was filtered and dried (19 gr of hydrogen sulfate of dodecylaminoacetonitrile). This product was slowly added in a flask of 250 ml to 60 cc of $H_2SO_4$. This solution was brought to 100° for 1.30 hour. After cooling, it was dropwise added to 400 ml of ice-cooled ethanol. The white precipitate which formed was filtered and recrystallized from ethanol.
MP (°C.): 190° (dec).

| Analysis | C | H | N |
|---|---|---|---|
| % calculated | 49.38 | 9.47 | 8.22 |
| % found | 49.30 | 9.55 | 8.15 |

EXAMPLE 5

(a) Synthesis of hexylaminoacetonitrile

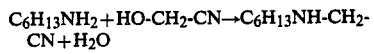

In a flask of 100 ml, 5.7 gr of hydroxyacetonitrile (0.1 mol) were mixed with 11 gr of hexylamine (0.11 mol) dissolved in 10 ml of MeOH. The temperature quickly raised during mixing. The solution was allowed to stand for 24 hours. The methanol was evaporated and the obtained liquid was distilled at 72° under 0.8 mm Hg.

(b) Synthesis of 2-n-hexylaminoacetamide 11.2 gr of hexylaminoacetonitrile (0.081 mol) were dropwise added to 31 ml of $H_2SO_4$ diluted in 30 ml of ice-cooled ethanol. After the addition was completed, ethanol was evaporated and 40 ml of $H_2SO_4$ were added to the white solid as obtained. This solution was heated for 1 hour at 100° C., then cooled and dropwise added to 200 ml of ice-cooled ethanol. The white precipitate which formed was filtered and washed with 50 ml of ethanol.
MP (°C.): 151-152.

| Analysis | C | H | N |
|---|---|---|---|
| % calculated | 37.49 | 7.87 | 10.93 |
| % found | 37.80 | 7.80 | 10.90 |

EXAMPLE 6

(a) Synthesis of 2-(n-pentylamino)butyronitrile

In a flask of 250 ml provided with a magnetic bar, 35 gr of $Na_2S_2O_5$ were dissolved in 95 ml of water. The ice-cooled solution was added with 14.9 gr of propionaldehyde (0.2 mol) and this new solution was stirred at 0° C. for 2 hours. A very slight precipitate formed. The solution was allowed to come back to room temperature before dropwise adding 23.9 ml of amylamine (0.2 mol). It was allowed to react for 2 hours and 13 gr of KCN (0.2 mol) were added on one portion. After 24 hours of reaction at room temperature, the solution was saturated with NaCl and extraction is made with ether. The ethereal phase was dried on $MgSO_4$ and added with a HCl solution in ether. The precipitate which formed was filtered and dried.
MP (°C.): 104°-105°.

(b) Synthesis of 2-(n-pentylamino)-butyramide

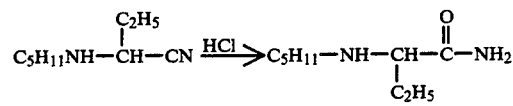

In a flask of 50 ml provided with a magnetic bar and ice-cooled, 1.9 gr (0.01 mol) of 2-(n-pentylamino)-valeronitrile were added to 17 ml of concentrated HCl. When the solid was completely dissolved, the solution was stored in a refrigerator for 24 hours. The hydrochloric acid was then evaporated by means of a rotary evaporation and the solution wax neutralized with a 1N NaOH solution. At pH=6, the solution was washed several times with benzene. At pH=11-12, the solution was extracted with ether; the ether extracts were combined, dried in $MgSO_4$ and evaporated. The residue as obtained was sublimed at 70° C. under $2.10^{-2}$ mm Hg
MP (°C.): 58-59.

| Analysis | C | H | N |
|---|---|---|---|
| % calculated | 62.75 | 11.7 | 16.26 |
| % found | 62.7 | 11.65 | 16.05 |

EXAMPLE 7

Synthesis of 2-(N-n-hexyl-N-methylamino)acetamide

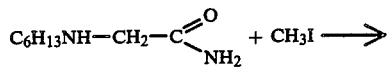

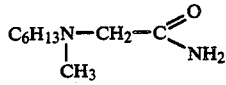

In a flask of 100 ml, 7.9 gr (0.05 mol) of 2-(n-hexylamino)acetamide and 7.8 gr (0.055 mol) of methyl iodide were mixed in 50 ml of methanol. This solution was left for 1 month at room temperature, then evaporated. The residue was dissolved in a 1N NaOH solution until basic pH and extracted with ether. The ether phase was dried on $MgSO_4$ and evaporated. The solid as obtained was chromatographed on a column of $SiO_2$ by eluting with a benzene-methanol mixture (7:3). The desired product was thus obtained.
MP (°C.)=64-65.

| Analysis | C | H | N |
|---|---|---|---|
| % calculated | 62.75 | 11.70 | 16.26 |
| % found | 63.10 | 11.32 | 16.12 |

EXAMPLE 8

Synthesis of 2-(N-benzyl-N-n-hexyl)aminoacetamide

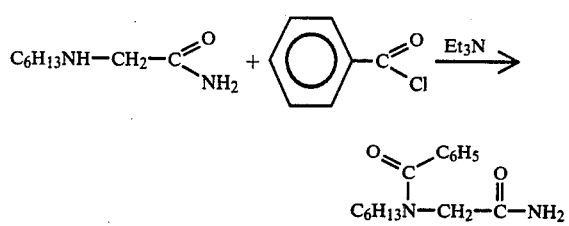

In a three necked flask of 258 ml provided with a magnetic bar, a thermometer, a dropping funnel and a cooler with a top calcium chloride tube, 100 ml of chloroform, 6.23 gr gr (0.04 mol) of 2-(n-hexylamido)acetamide and 8 ml (0.055 mol) of triethylamine are mixed. To this solution cooled at 10°, 5.1 ml (0.044 mol) of benzoyl chloride dissolved in 10 ml of chloroform were dropwise added. The reaction mixture was refluxed for 20 hours, cooled and washed three times with 1N HCl, once with water, twice with 1N NaOH and twice with water. The chloroform solution was dried on $MgSO_4$ and evaporated, the residue was crystallized from an ether-pentane mixture, then from cyclohexane.

MP (°C.): 97-98.

| Analysis | C | H | N |
|---|---|---|---|
| % calculated | 68.67 | 8.45 | 10.67 |
| % found | 68.7 | 8.25 | 10.60 |

EXAMPLE 9

Synthesis of N-n-hexyl-2-(n-hexylamino)acetamide

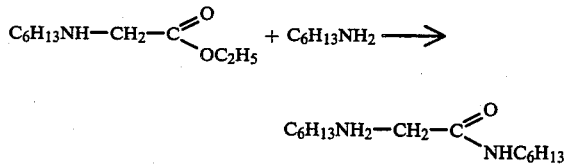

Into an autoclave, 5.6 gr (0.03 mol) of ethyl ester of 2-(n-hexylamino)acetic acid, 15 ml (0.1125 mol) of n-hexylamine and 1 mml of ethanol were added. The mixture was heated to 120° for 40 hours. The solvent and excess amine were then evaporated. The residue was solidified in pentene at low temperature ($-80°$ C.), recrystallized three times from hexane, then dissolved in ether and added with a saturated HCl solution in ether till acid pH. The hydrochloride was recrystallized from isopropanol.

MP (°C.): 158-159.

| Analysis | C | H | N |
|---|---|---|---|
| % calculated | 60.29 | 11.2 | 10.04 |
| % found | 60.44 | 11.03 | 9.92 |

EXAMPLE 10

Synthesis of 2-(n-hexylamino)acetamide

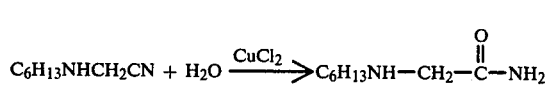

In an Erlenmeyer flask of 250 ml, 1 gr (0.072 mol) of n-hexylaminoacetonitrile, 1.22 gr (0.072 mol) of dehydrated cupric chloride and 100 ml of $H_2O$ were added. Ethanol was then added until obtention of a homogenous phase. The pH of the solution was adjusted to 10 by means of 1N NaOH and the reaction mixture was stirred for 4 hours at room temperature,; a purple solid was formed and was filtered, resuspended in ammoniac solution and extracted with dichloromethane. The organic phase was three times washed with water, dried on $K_2CO_3$ and evaporated. The residue was recrystallized from cyclohexane.

MP (°C.): 62-63

EXAMPLE 11

Synthesis of N-n-butyl-2-[N-acetyl-N(4-phenoxybutyl)]aminoisavaleramide

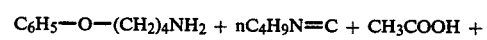

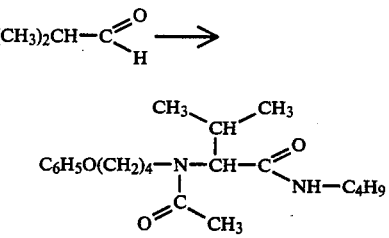

In a three-necked flask of 25 ml provided with a magnetic bar, a calcium chloride tube and a dropping funnel, 1.99 gr (0.012 mol) of phenoxybutylamine, 1 gr (0.012 mol) of n-butylisonitrile and 0.72 gr of acetic acid were mixed in 5 ml of methanol. A precipitate of phenoxybutylamine acetate formed. This suspension cooled in an ice bath was added under good agitation with 0.87 gr (0.012 mol) of isobutyraldehyde.

When the reaction mixture was back to room temperature, the precipitate was completely dissolved.

Stirring was still allowed at room temperature overnight (complete disappearance of the characteristic isonitrile odor). The methanol was then evaporated and the residual oil was taken up in 20 ml of a 5/1 hexane/benzene mixture. The solid which formed was filtered and the filtrate was evaporated and distilled at 185° C. under $4.10^{-2}$ mm Hg.

| Analysis. | C | H | N |
|---|---|---|---|
| % calculated | 69.58 | 9.45 | 7.73 |
| % found | 69.15 | 9.32 | 7.56 |

EXAMPLE 12

Synthesis of N-methyl-N-n-octyl-2-(N-methyl-N-n-octyl-)aminoacetamide

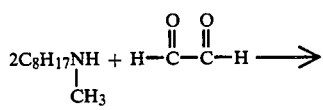

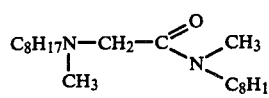

In a flask of 25 ml provided with a magnetic bar, 6 gr (0.0558 mol) of methyl-n-octylamine and 1.57 gr (0.0186 mol) of glyoxal hydrate were mixed. This solution was stirred for 3 hours at room temperature. 3.9 gr of potassium carbonate were then added, this suspension was stirred for 10 minutes and filtered. The obtained oil was heated for 1 hour at 100° C., then distilled. The fraction distilling between 150° and 157° C./0.03 mm Hg was dissolved in 50 ml of acidified water till pH=1 with diluted hydrochloric acid, and twice extracted with 20 ml of ether. The aqueous phase was neutralised and extracted with chloroform. The organic phase was dried in $K_2CO_3$ and evaporated. The residue was dissolved in ether and acidified with a solution of hydrochloric acid in ether. After one night at −2° C., a white product melting at 115°–116° C. was obtained.

| Analysis | C | H | N |
|---|---|---|---|
| % calculated | 66.17 | 11.94 | 7.72 |
| % found | 65.7 | 11.32 | 7.70 |

The melting points and the recrystallization solvents of derivatives according to the invention are listed in the following table I.

TABLE I

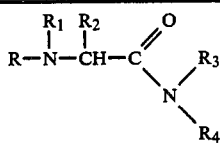

| No | R | $R_1$ | $R_2$ | $R_3$ | $R_4$ | F(°C.) | Recrystallization solvent |
|---|---|---|---|---|---|---|---|
| 1 | $nC_8H_{17}$ | H | H | H | H | 79 | acetone/cyclohexane |
| 2 | $nC_6H_{13}$ | H | H | H | H | 62–63 | cyclohexane |
| 3 | $nC_5H_{11}$ | H | H | H | H | 46 | cyclohexane |
| 4 | $HO(CH_2)_6$ | H | H | H | H | 96–97 | AcOEt |
| 5 | $HO(CH_2)_6$ | $CH_2C(=O)NH_2$ | H | H | H | 115 | isopropanol |
| 6 | $CH_3OC(=O)-(CH_2)_5$ | $CH_2-C(=O)NH_2$ | H | H | H | 116–117 | isopropanol |
| 7 | $HO-(CH_2)_4-$ | H | H | H | H | 81 | EtOH (1) |
| 8 | $CH_3OC(=O)-(CH_2)_5$ | H | H | H | H | 160 | MeOH (1) |
| 9 | $nC_7H_{15}$ | H | H | H | H | 69 | ether-pentane |
| 10 | $nC_{18}H_{37}$ | H | H | H | H | 103 | ether |
| 11 | $nC_9H_{19}$ | H | H | H | H | 79 | cyclohexane |
| 12 | $nC_6H_{13}$ | H | H | H | H | 152–153 | ethanol (2) |
| 13 | $nC_{12}H_{25}$ | H | H | H | H | 190(dec) | ethanol (2) |
| 14 | $nC_{10}H_{21}$ | H | H | H | H | 87 | cyclohexane |
| 15 | $CH_3OC(=O)-(CH_2)_7$ | H | H | H | H | 70–72 | AcOEt |
| 16 | $C_2H_5-OC(=O)-(CH_2)_7$ | H | H | H | H | 139–140 | EtOH (2) |
| 17 | $CH_3(CH_2)_7-CH=CH-(CH_2)_8$ | H | H | H | H | 85–87 | acetone |
| 18 | $C_7H_{15}-CH(CH_3)$ | H | H | H | H | 58–59 | pentane |

TABLE I-continued $$R-N(R_1)-CH(R_2)-C(=O)-N(R_3)(R_4)$$

| No | R | R₁ | R₂ | R₃ | R₄ | F(°C.) | Recrystallization solvent |
|----|---|----|----|----|----|--------|---------------------------|
| 19 | $C_8H_{17}$ | $C_6H_5-C(=O)-$ | H | H | H | 99 | cyclohexane |
| 20 | $C_5H_{11}$ | H | H | H | H | 151 | ethanol (2) |
| 21 | $(CH_3)_2CH(CH_2)_2CH(CH_3)-$ | H | H | H | H | 50–51 | hexane |
| 22 | $C_5H_{11}-CH(CH_3)-$ | H | H | H | H | 52–53 | pentane |
| 23 | $CH_3OC(=O)-(CH_2)_7-$ | $-CH_2-C(=O)NH_2$ | H | H | H | 125 | EtOH |
| 24 | $(CH_3)_2CH(CH_2)_3-CH(CH_3)-$ | H | H | H | H | 63 | pentane |
| 25 | $nC_6H_{13}$ | $C_6H_5-C(=O)-$ | H | H | H | 97–98 | cyclohexane |
| 26 | $nC_5H_{11}$ | H | H | H | H | 115–125 | ether (3) |
| 27 | $nC_6H_{13}$ | H | H | H | H | 207 | MeOH—Ether (1) |
| 28 | $nC_6H_{13}$ | $C_2H_5$ | H | H | H | 120–121 | MeOH—Ether (1) |
| 29 | $C_4H_9-CH(C_2H_5)-$ | H | H | H | H | 127–128 | Ethanol-Ether (1) |
| 30 | $nC_6H_{13}$ | $CH_3$ | H | H | H | 64–65 | Cyclohexane |
| 31 | $nC_6H_{13}$ | H | H | H | H | 142–147 | MeOH/Ether (4) |
| 32 | $nC_8H_{17}$ | $(CH_3)_3C-C(=O)-$ | H | H | H | 68–69 | pentane |
| 33 | $nC_5H_{11}$ | H | H | H | H | 205–207 | MeOH (1) |
| 34 | $nC_5H_{11}$ | H | H | H | H | 104–105 | acetone (3) |
| 35 | $nC_5H_{11}$ | H | H | H | H | 149–151 | MeOH (4) |
| 36 | $C_6H_5-(CH_2)_2$ | H | H | H | H | 90–91 | Ether-pentane |
| 37 | $nC_6H_{13}$ | H | H | $nC_6H_{13}$ | H | 158–159 | isopropanol (1) |
| 38 | $nC_6H_{13}$ | H | H | $CH_3$ | H | 183–184 | isopropanol (1) |
| 39 | $nC_6H_{13}$ | $-CH_2C(=O)NH_2$ | H | H | H | 183 | ethanol (1) |
| 40 | $CH_2=CH(CH_2)_5$ | H | H | H | H | 51 | ether |
| 41 | $nC_5H_{11}$ | H | $CH_3$ | H | H | 71–72 | sublimation |
| 42 | $HXC-C(CH_3)_2-$ | H | H | H | H | 75 | ether |
| 43 | $nC_{10}H_{21}$ | H | H | H | H | 195–210 | ethanol (2) |
| 44 | $nC_8H_{17}$ | $C_2H_5$ | H | H | H | 47–48 | pentane |

TABLE I-continued $$R-\underset{R_1}{N}-\underset{R_2}{CH}-\underset{}{\overset{O}{C}}-\underset{R_4}{\overset{R_3}{N}}$$

| No | R | $R_1$ | $R_2$ | $R_3$ | $R_4$ | F(°C.) | Recrystallization solvent |
|---|---|---|---|---|---|---|---|
| 45 | $nC_6H_{13}$ | $(CH_3)_3C-\overset{O}{\underset{}{C}}$ | H | H | H | 15 | pentane |
| 46 | $nC_5H_{11}$ | H | $C_6H_5$ | H | H | 100–101 | cyclohexane |
| 47 | $nC_6H_{13}$ | $C_2H_5-O-\overset{O}{\underset{}{C}}$ | H | H | H | 52–53 | pentane |
| 48 | $nC_5H_{11}$ | H | $C_2H_5$ | H | H | 58–59 | cyclohexane |
| 49 | ⌬—$(CH_2)_3$ | H | H | H | H | 215–218 | MeOH (1) |
| 50 | $CH_2=CH-(CH_2)_6$ | H | H | H | H | 63 | AcOEt/pentane |
| 51 | $HOOC(CH_2)_7$ | H | H | H | H | 144–145 | Acetone/$H_2O$ (1) |
| 52 | ⌬—$(CH_2)_4$ | H | H | H | H | 208–210 | ethanol (1) |
| 53 | $nC_6H_{13}$ | H | H | ⌬—Cl | H | 260–265 decomp. | acetone (1) |
| 54 | $nC_6H_{13}$ | H | H | $CH_3$ | $CH_3$ | 115°/4.10$^{-2}$ mmHg | |
| 55 | ⌬—$O-(CH_2)_4$ | $CH_3C\overset{O}{\underset{}{\diagdown}}$ | $(CH_3)_2CH$ | $C_4H_9$ | H | 185°/4.10$^{-2}$ mmHg | |
| 56 | (⌬)$_2CH-(CH_2)_2-$ | H | H | H | H | 106 | acetone-pentane |
| 57 | ⌬—$O-(CH_2)_2$ | H | H | H | H | 209–211 | ethanol (1) |
| 58 | $(C_2H_5O)_2CH-(CH_2)_3$ | H | H | H | H | 152°/2.10$^{-2}$ mmHg | |
| 59 | ⌬—$(CH_2)_2$ | H | H | ⌬ | H | 290–292(dec) | methanol (1) |
| 60 | $nC_6H_{13}$ | H | H | ⌬ | H | 258–260(dec) | methanol-acetone (1) |

TABLE I-continued

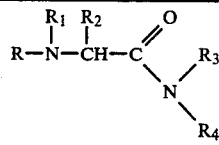

| No | R | $R_1$ | $R_2$ | $R_3$ | $R_4$ | F(°C.) | Recrystallization solvent |
|----|---|-------|-------|-------|-------|--------|---------------------------|
| 61 | $nC_8H_{17}$ | $nC_8H_{17}$ | H | H | H | 47 | hexane |
| 62 | $nC_8H_{17}$ | $CH_3$ | H | $nC_8H_{17}$ | $CH_3$ | 115–116 | ether (1) |

(1) = HCl
(2) = $H_2SO_4$
(3) = benzoate
(4) = $H_3PO_4$

Pharmacological and biochemical results of compounds according to the invention are given in table II also enclosed. In this table, numbers in column 1 correspond to numbers of column 1 of table I. The results given in this table are to be interpreted as follows.

The anticonvulsive effect was examined for tonic convulsions induced by bicuculline. The compounds of the invention were administrated orally at dosages of 10 and 100 mgr/kg, each to 5 mice, 3 hours before intravenous injection of bicuculline at the dosage of 0.6 mgr/kg. The number of mice protected against tonic convulsions and the number of dead mice were noted. The results are given as a score which represents the sum of animals protected by dosages of 10 and 100 mgr/kg of the compounds.

The $LD_{50}$ values were calculated according to the Lichtfield and Wilcoxon method (J. Pharmacol. Exp. Ther. 96, 99, 1949) and expressed in mgr/kg. The products were orally administered to mice.

The effect on behaviour was studied by using a method deriving from that of S. Irwin (Gordon Res. Conf. on Medicinal Chem., 133, 1959). The substances suspended in a 1% tragacanth gum mucilage were orally administered by means of an intragastric tube to groups of 5 male mice (CD1, Charles River strain, fasted from 18 hours). If the available amount of drug allows it, the doses are 3000, 1000 and 300 mgr/kg. In the case of the latter doses being active, the effect of the drug is examined at 100, 30, 10 and if possible 3 mgr/kg. The behaviour was studied 2, 4, 6 and 24 hours after treatment. The observation was extended if symptoms persisted at this moment. The deaths were registered for 14 days following the treatment. None of the tested products has induced an abnormal behaviour in mice. It has in particular to be noted that they are free of sedative effects.

TABLE II

| | BIOLOGICAL RESULTS. | |
|---|---|---|
| | bicuculline | $DL_{50}$ mg/kg |
| 1 | 4 | 2220 |
| 2 | 4 | 780 |
| 3 | 7 | 1925 |
| 4 | 4 | >3000 |
| 5 | 2 | >3000 |
| 6 | 6 | >3000 |
| 7 | 2 | |
| 8 | 1 | >3000 |
| 9 | 5 | 1425 |
| 10 | 1 | >3000 |
| 11 | 2 | 1950 |
| 12 | 5 | 2800 |
| 13 | 2 | >3000 |
| 14 | 6 | 2600 |

TABLE II-continued

| | BIOLOGICAL RESULTS. | |
|---|---|---|
| | bicuculline | $DL_{50}$ mg/kg |
| 15 | | |
| 16 | 5 | >1000 |
| 17 | 2 | >3000 |
| 18 | 2 | >1000 |
| 19 | 2 | 3000 |
| 20 | 1 | >1000 |
| 21 | 3 | 640 |
| 22 | 5 | 640 |
| 23 | 7 | >1000 |
| 24 | 5 | 650 |
| 25 | 5 | 3660 |
| 26 | 3 | 1950 |
| 27 | 4 | 860 |
| 28 | 5 | 435 |
| 29 | 4 | 1950 |
| 30 | 4 | 570 |
| 31 | 6 | 1650 |
| 32 | 5 | >3000 |
| 33 | 6 | 2880 |
| 34 | 5 | >3000 |
| 35 | 3 | >3000 |
| 36 | 7 | |
| 37 | 3 | |
| 38 | 3 | |
| 39 | | |
| 40 | 4 | |
| 41 | 4 | |
| 42 | 6 | |
| 45 | 3 | |
| 46 | 5 | |
| 47 | 8 | |
| 48 | 6 | |
| 49 | 7 | |
| 50 | 6 | |
| 51 | 6 | |
| 52 | 7 | |
| 53 | 4 | |
| 54 | 4 | |
| 55 | 6 | |
| 56 | 4 | |
| 57 | 5 | |

The substances of the invention have the property of inhibiting convulsions induced by biccullne in mouse. This effect indicates that these substances have an antiepileptic potential, probably by acting on the GABA system. As a matter of fact, bucuculline is a specific antoganist of GABA. Besides, the effect of the products on the activity of the GABA synthesis enzyme, decarboxylase glutamate (GAD), was studied. The activity of the GAD was determined in homogenizates of rat brain according to the method described by L. Parker (Methods in Enzymology, Ed. S. Fleischer, 1974, Vol. XXXII, part V., p. 779). The tested products were added at a final concentration of $10^{-4}$M. In general the products of the invention revealed as active in this test. Products n° 3, 8, 17 and 33 were particularly remarkable in this respect. In general, the products of the invention increase the activity of the GAD transaminase (GABA-T), enzyme of GABA catabolism, which results in an increase of the GABA levels at the level of GABA-ergic neurons.

Amongst the substances according to the invention, 2-n-pentylaminoacetamide and its hydrochloride were more particularly studied. The results are partly given by table III. These products inhibit convulsions induced by bicuculline in mouse: the ED50 values are 11.2 and 5.74 mgr/kg per os respectively. The hydrochloride was also administered intravenously. In this case, ED50 value is 2.19 mgr/kg. This value is not significantly lower than that after oral administration, indicating an excellent absorption from the intestinal tractus. Table III also gives the therapeutical index (LD50/ED50). Amongst compounds of the invention, this therapeutical index is higher than those of valproate, diphenylhydantoin and phenobarbital.

TABLE III

Mouse: Convulsions induced by bicuculline (0.6 mgr/kg intravenously) Treatment 3 hours before induction of convulsions.

| Treatment | $DL_{50}$ mgr/kg | $DE_{50}$ mgr/kg | $DL_{50}/DE_{50}$ |
|---|---|---|---|
| 2-n.pentylamino-acetamide | 1925 | 11,2 | 172 |
| 2-n.pentylamino-acetamide Hcl | 2240 | 5,74 | 390 |
| Na Valproate | 1250 | 89,1 | 14 |
| Na Diphenylhydantoin | 320 | 2,63 | 122 |
| Na Phenobarbital | 185 | 2,11 | 88 |

As valproate, 2-n-pentylaminoacetamide is inactive against convulsions induced by strychnine. Its anticonvulsive action does not seem to be medullar but central.

Furthermore, 2-n-pentylaminoacetamide and its hydrochloride seem to act at the level of GABA receptors specifically. This is indicated by the following results.

(1) its antagonist action against convulsions due to bicuculline may be overcome by an increase of the bicuculline doses.

(2) 2-n-pentylaminoacetamide only slightly inhibits convulsions due to leptazol in mouse, (3) 2-n-pentylaminoacetamide hydrochloride has no effect on the convulsions due to picrotoxine.

As a matter of fact, leptazol does not act at the level of the GABA receptors and picrotoxine acts on the site adjacent to the GABA receptor but not directly on it. Moreover, 2-n-pentylaminoacetamide competes with bicuculline, namely the specific antagonist of GABA. The interaction of 2-n-pentylaminoacetamide hydrochloride with the GABA system is confirmed by the fact that, when administered at 200 mgr/kg per os in rat, this product potentiates the GAD activity by 26% without modifying that of the GABA-T; the GABA rate of the black substance, structure rich in GABA-ergic terminations, is increased by 28,33 and 38% respectively two, three and 4 hours after treatment.

2-n-Heptylaminoacetamide has the property to protect mice against mortality caused by KCN. This activity very likely explains itself by an effect on the cerebral energetic metabolism during anoxia. This effect on the cerebral energetic metabolism has been confirmed for 2-n-pentylaminoacetamide hydrochloride in a series of experiments on cerebral anoxia caused by decapitation of rat. It has thus been proved that this product prevents accumulation of lactate in the brain during the first seconds of anoxia.

Furthermore, n-2-pentylaminoacetamide potentiates the effects of 1-trypthophan in mouse, indicating a facilitation of the central serotoninergic system and thus the existence of psychotropic properties, in particular antidepressive properties.

In other respects, 2-n-octylaminoacetamide (50 mgr/kg intraperitoneally) has been studied in an experiment of passive prevention in mouse, wherein it has delayed the behaviour extinction. This product and very likely other compounds of the invention thus improve mnesic retention.

Some compounds of the invention inhibit platelet agglutination in human plasma. The measure of the inhibition of platelet agglutination is made according to the turbidimetric method of G. V. R. Born and M. J. Cross (J. Physiol. 168, 178, 1973). The plasma rich in platelets is preincubated for 3 minutes before introduction of the inductor agent, Trombofax. The inhibon of the maximum amplitude of agglutination is measured by means of Upchurch agglutometer. In this test, compounds 1, 11, 14 and 18 have shown as being active.

Thus 2-n-pentylaminoacetamide and its hydrochloride act on the GABA-ergic system by promoting the GABA transmission as shown by antagonism of the bicuculline effect. This effect could result from an activation of GAD. These products would thus be more particularly indicated for treatment of epilepsy and dyskinesiae such as parkinsonism, this syndrome very likely resulting from an insufficiency of the GABA system. The activity on the cerebral energetic metabolism and anoxia also allows to contemplate use of this product for cerebral ischemic diseases. Moreover, the effect of the 2-n-octylaminoacetamide in the memory test and the effect of the 2-n-pentylaminoacetamide on the serotininergic system allow to propose an additional indications for the compounds of the invention mnesic troubles and some psychiatric affections, such as depression.

For administration of the new compounds of the invention, the daily dose will be 10 mgr to 2 gr, the unit dose being 10 to 300 mgr. Due to the very low toxicity of the products according to the invention, the doses such as mentioned may be increased without danger.

The products of the invention may be used as various galenic forms. Following examples are not limitative and concern galenic formulations containing an active product designated by A.

This active product is one of the following compounds:
2-n-pentylaminoacetamide,
2-n-octylaminoacetamide,
Methyl 6-(dicarboxamidomethyl)aminohexanoate,
2-n-decylaminoacetamide,
Methyl 8-(dicarboxamidomethyl)aminooctanoate,
2-n-hexylaminoacetamide,
2-(2-phenylethyl)aminocacetamide,
2-n-octadecen-9-ylaminoacetamide,
2-(N-carboxamidomethyl-N-n-hexyl)aminoacetamide,
2-(1,1-dimethylpropyn-2-yl)aminoacetamide,
Ethyl N-n-hexyl-N-carboxamidomethylcarbamate,
2-n-pentylaminobutyramide,
2-(3-phenylpropyl)aminoacetamide,
2-octen-7-ylaminoacetamide,
8-carboxamidomethylaminooctanoic acid,
2-(4-phenylbutyl)aminoacetamide, N-butyl-2-N-acetyl-N-(4-phenoxybutyl)aminoisovaleramide.

| Tablets. | |
|---|---|
| A | 300 |
| starch Sta-Rx 1500 | 180 mgr |
| Calcium phosphate | 100 mgr |
| aerosil | 5 mgr |
| Magnesium stearate | 15 mgr |
| A | 100 mgr |
| Corn starch | 100 mgr |
| lactose | 80 mgr |
| aerosil | 5 mgr |
| talc | 5 mgr |
| Magnesium stearate | 10 mgr |
| Capsules. | |
| A | 50 mgr |
| lactose | 110 mgr |
| Corn starch | 20 mgr |
| gelatin | 8 mgr |
| Magnesium stearate | 12 mgr |
| A | 200 mgr |
| polyvinylpyrrolidone | 10 mgr |
| Corn starch | 100 mgr |
| Cutina HR | 10 mgr |
| IM or IV injectables. | |
| A | 100 mgr |
| Sodium chloride | 20 mgr |
| Sodium acetate | 6 mgr |
| Distilled water for injectables | 5 ml |
| IM injectables. | |
| A | 200 mgr |
| Benzyl benzoate | 1 gr |
| Oil for injection, ad | 5 ml |
| Syrup. | |
| A | 5 gr |
| Ammonium glycyrhizinate | 0.5 gr |
| atric acid | 0.5 gr |
| nipasept | 0.1 gr |
| saccharose | 70 gr |
| flavouring agent | 0.1 gr |
| water, ad | 100 ml |
| Solute. | |
| A | 2 gr |
| sorbitol | 50 gr |
| Glycerin | 10 gr |
| anise essence | 0.1 gr |
| propylene glycol | 10 gr |
| demineralized water | 100 mgr |

| -continued | |
|---|---|
| Suppositories. | |
| A | 250 mgr |
| butylhydroxyanisole | 10 mgr |
| semi-synthetic glycerides, ad | 3 gr |

We claim:

1. A pharmaceutical composition containing as the active ingredient an effective amount, for the treatment of epilepsy, dyskinesiae, memory troubles and psychic troubles, of a glycinamide derivative of the formula:

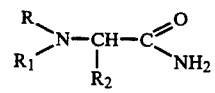

wherein:
R is a linear pentyl group, or a linear or branched $C_2-C_5$ alkyl group substituted by at least one phenyl group or at least one halo-substituted phenyl group,
$R_1$ is hydrogen, and
$R_2$ is hydrogen,
or the non-toxic, pharmaceutically acceptable acid addition salt thereof together with a pharmaceutically acceptable carrier or diluent.

2. The pharmaceutical composition according to claim 1 wherein the halo phenyl is substituted with a fluorine, bromine or chlorine atom.

3. The pharmaceutical composition according to claim 1 in a unit dose containing from 10 to 300 mg. of said glycinamide derivative.

4. A pharmaceutical composition containing as the active ingredient an effective amount of 2-n-pentylaminoacetamide, for the treatment of epilepsy, dyskinesiae, memory troubles and psychic troubles, or the non-toxic, pharmaceutically acceptable acid addition salt thereof together with a pharmaceutically acceptable carrier or diluent.

5. A pharmaceutical composition in unit dose form for treating tonic convulsions containing from 10 to 300 mg. of the glycinamide derivative of claim 4.

* * * * *